(12) United States Patent
Kolahi et al.

(10) Patent No.: US 7,343,822 B2
(45) Date of Patent: Mar. 18, 2008

(54) METHOD FOR OPERATING A MASS FLOW METER

(75) Inventors: Kourosh Kolahi, Kiel (DE); Thorsten Schröder, Gifhorn (DE); Ralf Storm, Essen (DE)

(73) Assignee: Krohne AG, Basel (CH)

( * ) Notice: Subject to any disclaimer, the term of this patent is extended or adjusted under 35 U.S.C. 154(b) by 182 days.

(21) Appl. No.: 11/258,698

(22) Filed: Oct. 26, 2005

(65) Prior Publication Data

US 2006/0096390 A1    May 11, 2006

(30) Foreign Application Priority Data

Oct. 29, 2004   (DE) .................. 10 2004 053 010
Nov. 22, 2004   (DE) .................. 10 2004 056 235

(51) Int. Cl.
*G01F 1/84* (2006.01)

(52) U.S. Cl. .................................. 73/861.357

(58) Field of Classification Search ........... 73/861.357, 73/861.355, 861.356
See application file for complete search history.

(56) References Cited

U.S. PATENT DOCUMENTS

| 5,027,662 | A | 7/1991 | Titlow et al. |
| 5,576,500 | A | 11/1996 | Cage et al. |
| 5,728,952 | A | 3/1998 | Yao et al. |
| 5,831,178 | A | 11/1998 | Yoshimura et al. |
| 6,763,730 | B1 | 7/2004 | Wray |
| 7,040,181 | B2 * | 5/2006 | Rieder et al. .......... 73/861.357 |
| 2003/0070495 | A1 | 4/2003 | Kolahi et al. |

OTHER PUBLICATIONS

Kourosh Kolahi, Cooperative Sensor Fusion in the Mass Flow Measurement and in the Production of Micro Organisms, Technishes Messen 71 (2004) 4, Oldenbourg Verlag, pp. 154-163.
Thorsten Schröder et. al., A Novel Control Algorithm for Coriolis Mass Flowmeters, Technisches messes 71 (2004) 4, Oldenbourg Verlag, pp. 259-267.

* cited by examiner

*Primary Examiner*—Jewel Thompson
(74) *Attorney, Agent, or Firm*—Cesari and McKenna, LLP

(57) ABSTRACT

A method for operating a mass flowmeter that employs the Coriolis principle and through which flows a medium, wherein the mass flowmeter incorporates a measuring tube that can be stimulated to oscillate, the measuring tube is stimulated to oscillate at a minimum of two mutually different frequencies and/or in at least two mutually different natural oscillating modes, and the resulting oscillations of the measuring tube are recorded. The density of the medium flowing through the measuring tube is determined by evaluating the acquired oscillations of the measuring tube on the basis of a physical-mathematical model for the dynamics of the mass flowmeter. In this fashion, highly accurate measurements are obtained for determining the density of the medium flowing through the measuring tube.

15 Claims, 2 Drawing Sheets

METHOD FOR OPERATING A MASS FLOW METER

BACKGROUND OF THE INVENTION

Field of the Invention

This invention relates to a method for operating a mass flowmeter that employs the Coriolis principle and encompasses a measuring tube through which flows a medium, whereby the measuring tube is energized to oscillate at a minimum of two mutually different frequencies and/or in at least two mutually different natural oscillating modes, and the resulting oscillations of the measuring tube are measured.

A similar method has been described earlier for instance in DE 100 02 635 A1. According to that document, the measuring tube is stimulated in three mutually different oscillating modes, and by means of the recorded oscillatory response pattern of the measuring tube, the characteristic values of the mass flowmeter such as its zero point and its sensitivity are determined, in real-time during the operation of the mass flowmeter, with the aid of a mathematical-physical model.

Determining the zero point and sensitivity as the characteristic values during the operation of the mass flowmeter essentially serves the purpose of improving the accuracy of the mass flow measurements. But with a Coriolis-type mass flowmeter it is additionally possible to measure the density of the medium flowing through the measuring tube. One approach frequently employed to that effect in conventional mass flowmeters has been to determine the density of the flowing medium by way of the natural frequency in the first oscillating mode of the vibrating measuring tube conducting the medium, with certain corrections made by means of thermal and/or voltage variables that are acquired with the aid of thermal sensors and, respectively, strain gauges mounted on the measuring tube and/or on a support pipe, if provided. It has been found, however, that density measurements of the medium flowing through the measuring tube, based on its natural frequency—here also referred to as resonant frequency—are often insufficiently accurate.

SUMMARY OF THE INVENTION

It is therefore the objective of this invention to introduce a method for operating a mass flowmeter by means of which the density of the medium flowing through the measuring tube can be determined with a high degree of accuracy.

Expanding on the above-described method for operating a mass flowmeter, this objective is achieved by determining the density of the medium flowing through the measuring tube in that the detected oscillations of the measuring tube are evaluated with the aid of a physical-mathematical model for the dynamics of the mass flowmeter.

Thus, according to the invention, the oscillatory response of the measuring tube, when stimulated, is recorded at the said minimum of two mutually different frequencies and/or in at least two mutually different resonant oscillating modes so that, with the aid of a physical-mathematical model for the dynamics, or oscillating pattern, of the mass flowmeter, it is possible to derive information on the density of the medium flowing through the measuring tube.

While the physical-mathematical model for the dynamics of the mass flowmeter is to encompass at least the dynamics of the oscillating measuring tube, it can additionally represent other constituent devices of the mass flowmeter as well.

Thus, in a preferred embodiment of the invention, the physical-mathematical model serving to determine density values is not only based on the dynamics of the measuring tube but also factors-in the effect of at least one other component of the measuring tube system, such as a support pipe and/or the measuring-tube suspension of the mass flowmeter. In this case, factoring-in additional components of the mass flowmeter in building the physical-mathematical model for the dynamics of the mass flowmeter provides a more complete representation of the actual device which, on the other hand, because of the more complex model, entails a greater processing effort.

For the purposes of this invention, it is entirely possible to use different physical-mathematical models. A preferred embodiment of the invention, however, employs at least a second-order physical-mathematical model for the dynamics of the mass flowmeter, for instance identical or similar to the one disclosed in the above-mentioned DE 100 02 635 A1. Specifically in this connection, a preferred embodiment of the invention ensures the capability of the physical-mathematical model to describe the oscillations of the mass flowmeter upon excitation of the measuring tube in its first and/or its second natural oscillating mode. In addition, a preferred implementation of the invention provides for the physical-mathematical model, in its density determination, to take into account the coupling between the first and the second resonant oscillating modes of the measuring tube oscillations. In another preferred embodiment of the invention, the physical-mathematical model also factors-in the third resonant oscillating mode and its coupling with the other lower-order resonant oscillating modes.

As has been explained further above, merely considering the resonant frequency of the measuring tube for determining the density of the medium flowing through the measuring tube gives rise to substantially unreliable measurements. In developing the invention it has been found that this is largely attributable to changes of the elasticity constant of the measuring tube due to extraneous factors to which it is exposed, such as thermal effects or mechanical stress. Therefore, a preferred version of the invention provides for the physical-mathematical model to reflect the effect of the elasticity constant of the measuring tube at any time during operation. Accordingly, in a preferred embodiment of the invention, the physical-mathematical model should encompass parameters representative of the stiffness, and thus the elasticity constant, of the measuring tube. These parameters implicitly describe the effect of the process conditions such as temperature, pressure and/or mechanical stress on the measuring tube and its stiffness.

There are various ways to stimulate the measuring tube to oscillate and to capture the resulting oscillatory responses of the measuring tube for determining the density of the medium flowing through the measuring tube with the aid of a physical-mathematical model. In a preferred embodiment of the invention, the measuring tube is operationally stimulated in its first natural oscillating mode by means of a first frequency for mass flow measurements, and by an additional excitation of the measuring tube in its first natural oscillating mode at a second frequency different from the first frequency, the resonant frequency of the measuring tube is measured in its first natural oscillating mode, and the density of the medium flowing through the measuring tube is determined via the effective oscillating mass in the first natural oscillating mode based on the resonant frequency of the measuring tube in that first natural oscillating mode and on the oscillations of the measuring tube resulting from the additional excitation of the measuring tube.

The term "operationally stimulated" used above and further below refers to the stimulation of the measuring tube that is required for the actual mass flow measurement, i.e. to generate Coriolis oscillations which in conventional fashion provide information on the mass flow through the measuring tube. The term "additional excitation" as used above and further below refers to the generation of oscillations of the measuring tube that do not serve to measure the mass flow proper but to permit density measurements based on the oscillatory response of the measuring tube to such additional excitation and evaluated with the aid of the physical-mathematical model.

In another form of implementation of the invention, a first additional excitation of the measuring tube takes place in its first natural oscillating mode at a first frequency and a second additional excitation of the measuring tube takes place in its first natural oscillating mode at a second frequency different from the first frequency, and the density of the medium flowing through the measuring tube is determined based on the effective oscillating mass in the first natural oscillating mode by way of the detected oscillations of the measuring tube that result from the two additional excitations of the measuring tube. Thus, in this preferred conceptual implementation, it means that, initially, there is only additional excitation and no operational stimulation. Hence, applying the above definitions of "additional excitation" and "operational stimulation", only density measurements are being performed in this case.

However, in a preferred embodiment of the invention, it is possible for mass flow measurements to also provide for an additional excitation of the measuring tube in its first natural oscillating mode at a third frequency that differs from the first and, respectively, from the second frequency and to determine the density of the medium flowing through the measuring tube based on the effective oscillating mass in the first natural oscillating mode by additionally factoring-in the resonant frequency of the measuring tube in its first natural oscillating mode. Accordingly, mass flow measurements can take place concurrently with density measurements.

In another embodiment of the invention, a first additional excitation of the measuring tube takes place in its second natural oscillating mode at a first frequency and a second additional excitation of the measuring tube takes place in its second natural oscillating mode at a second frequency different from the first frequency, and the density of the medium flowing through the measuring tube is determined based on the effective oscillating mass in the second natural oscillating mode by way of the detected oscillations of the measuring tube that result from the two additional excitations of the measuring tube.

In a preferred implementation of the invention, an operational stimulation of the measuring tube in its first natural oscillating mode takes place at a third frequency that differs from the first and, respectively, second frequency and the density of the medium flowing through the measuring tube is determined based on the effective oscillating mass in the second natural oscillating mode by additionally factoring-in the resonant frequency of the measuring tube in its first natural oscillating mode.

The above statement to the effect that for determining the density of the medium flowing through the measuring tube the resonant frequency of the measuring tube in its natural oscillating mode is also factored in, reflects an established approach used even in conventional Coriolis mass flowmeters in which the density of the medium flowing through the measuring tube is determined on the basis of only the natural oscillating mode of the measuring tube, perhaps with temperature and/or stress compensation.

It is therefore unnecessary at this point to explain how the natural (resonant) frequency of the measuring tube is determined.

In a preferred embodiment of the invention, designed to permit the inclusion of all the capabilities referred to above, the temperature in the mass flowmeter is measured to allow compensation for the temperature dependence of the function of at least one component of the mass flowmeter system, such as an oscillation generator for the measuring tube and/or an oscillation sensor for the measuring tube. This allows correction for thermal effects in the density measurements that would not otherwise be included in the physical-mathematical model.

Another preferred embodiment of the invention also provides for the temperature of the measuring tube to be gauged so as to permit compensation in the density measurements for a thermally induced change in the volume of the measuring tube. Finally, in a preferred implementation of the invention, the pressure inside the measuring tube is determined so as to permit compensation in the density measurements for pressure-related changes in the volume of the measuring tube. It is thus possible to further improve the accuracy in measuring the density of the medium flowing through the measuring tube. In the preferred implementation of the invention last mentioned, pressure measurements can be performed in direct fashion using a pressure sensor or indirectly, for instance by monitoring the elastic constant of the measuring tube.

There are numerous ways in which the novel method for operating a mass flowmeter can be configured and further enhanced. In this context, attention is invited to the dependent claims and to the following detailed description of preferred embodiment of the invention with reference to the attached drawings

DESCRIPTION OF THE PREFERRED EMBODIMENTS

Figure 1:
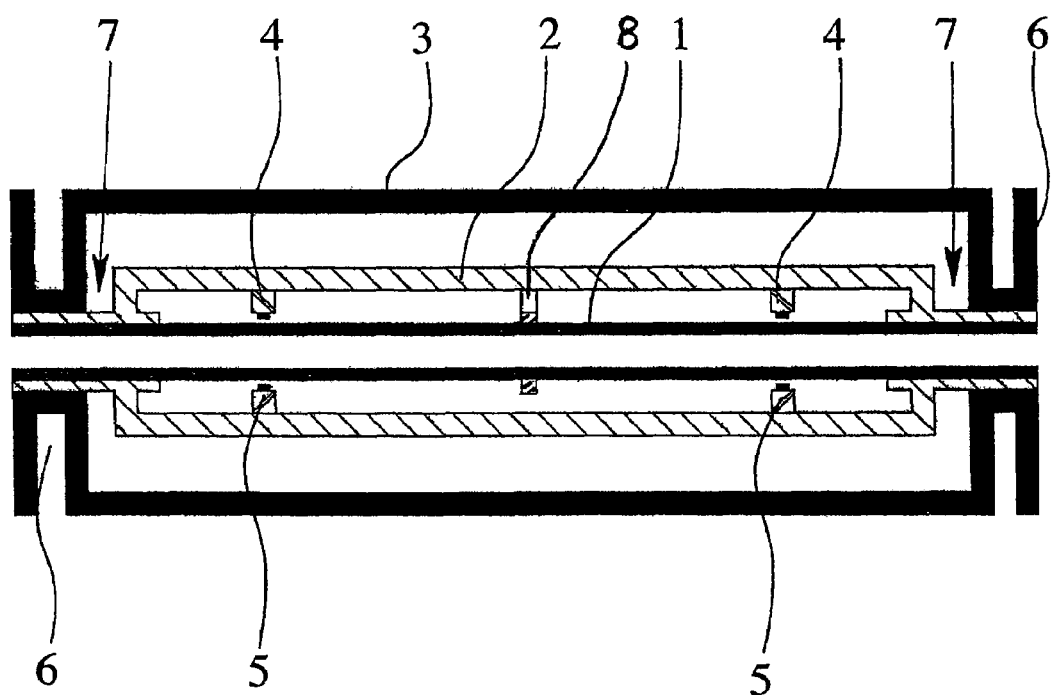
FIG. 1 shows in longitudinal section the mechanical structure of a Coriolis mass flowmeter designed for use with the preferred embodiments of the invention.

Conventional mass flowmeters employing the Coriolis principle are often operated by the natural self-resonance method. This also permits measuring the density of the medium flowing through the measuring tube. The measuring base is the assumed model for an oscillating elastic mass system where the radian frequency $\omega_O$ is:

$$\omega_0 = \sqrt{\frac{c}{m}} \tag{1}$$

where c is the effective elasticity constant of the oscillator and its mount and m is the effective oscillating mass. This oscillating mass is composed of the oscillator itself and of its content, if any, and thus:

$$m = m_P + m_F \qquad (2)$$

If in the case of the measuring tube of a Coriolis mass flowmeter the content consists of a flowing medium, the mass $m_F$ of the medium is equal to the product of its density $\rho_F$ and the volume $V_F$ of the measuring tube;

$$m_F = \rho_F V_F \qquad (3)$$

If one substitutes for the oscillating mass the effective mass of the empty oscillator $m_P$ and of the flowing medium, the result will be the following defining equation for determining the density of the flowing medium as a function of its natural frequency:

$$\rho_F = \frac{c}{V_F} \omega_0^{-2} - \frac{m_P}{V_F} \qquad (4)$$

The parameters in this defining equation include the mass of the empty oscillator, the volume of the measuring tube and the effective elasticity constant of the oscillator. The parameters, when viewed as constants, would allow the characteristic curve of the density measurement to be established by measuring the natural self-frequency for two different density values.

In reality, the parameters of the defining Equation (4) cannot be assumed to constitute constants, for the following reasons:

1. The elasticity constant c is composed of the elasticity constants of the oscillator components, the measuring tube, the support pipe if any, etc. It is a function of the applicable module of elasticity of the components, their shape and their positions. It therefore depends not only on the temperature but on the temperature gradients as well. Moreover, the elasticity constants of the oscillator components are subject to change due to mechanical stress and tension gradients as well as numerous process variables such as temperature, pressure, ground potential and viscosity. Then, too, the oscillation amplitude and mode have an effect on elasticity.

In summary, the elasticity constant is a function of numerous process and measuring parameters so that:

$$c = f(T, \Delta T, \sigma, \Delta \sigma, P, \dot{m}, \hat{x}, \text{Formulation}, \ldots) \qquad (5)$$

This functional interrelationship between the mentioned variable factors and the elasticity constant is very complex and can only to a limited extent be expressed in analytical terms, making any allowance for the effective stiffness with the aid of auxiliary sensors and applying the defining Equation (5) or a variation thereof, as much a complex and incomplete solution as in the case of conventional mass flowmeter employing temperature sensors or strain gauges.

2. The effective oscillating mass m is composed of the respective effective oscillating mass of the oscillator components, the measuring tube, the support pipe, the fluid medium, etc. This effective oscillating mass depends on process variables such as temperature, pressure, viscosity, fluid composition as well as the oscillation amplitude, the oscillation frequency and the oscillation mode, which, in turn, leads to a frequency dependence. This means that, for instance in the case of resonant frequencies of the measuring tube, it is primarily the measuring tube and its content that contribute to the effective oscillating mass, whereas in the case of the resonant frequencies of the suspension, the contribution of the measuring tube and its content is marginal, so that at these frequencies the sensitivity of the density measurements tends toward zero. In conventional mass flowmeters employing the Coriolis principle, this frequency dependence can only partially be compensated for even with such complex structural provisions as torsional oscillators or constant spacing of the resonant frequencies.

3. The parameter "measuring tube volume" V in the conditional density equation depends on the process pressure, mechanical stress on the measuring tube and the temperature of the measuring tube.

In principle, the density of the medium flowing through the measuring tube is to be measured independent of the influence of the actually effective elastic rigidity and independent of the actually effective measured volume. As explained further above, this is accomplished by stimulating the measuring tube at a minimum of two mutually different frequencies and measuring the resulting oscillations of the measuring tube, while the density of the medium flowing through the measuring tube is determined by evaluating the recorded oscillations of the measuring tube on the basis of a physical-mathematical model for the dynamics of the mass flowmeter. In other words, the essential idea of the invention consists in executing the targeted excitation of the mass flowmeter and the evaluation of the oscillatory responses on the basis of a model in such fashion that the effective elastic rigidity of the mass flowmeter has no bearing on the density measurement. The effective elastic rigidity is also used, in conjunction with the temperature, for correcting the actually effective measured volume.

The following explanatory description of preferred embodiments of the invention refers to a Coriolis mass flowmeter mechanically designed as depicted in FIG. 1. It should be noted that the method according to the invention, including the preferred embodiment of the invention described below, is not limited to a Coriolis mass flowmeter of the design shown in FIG. 1. On the contrary, essentially any tube geometries including dual-tube configurations are possible.

The FIG. 1 Coriolis mass flowmeter encompasses a measuring tube 1, a support pipe 2, a protective tube 3, two oscillation generators 4 and two oscillation sensors 5. The one measuring tube 1 is of a straight linear design and the Coriolis mass flowmeter depicted in FIG. 1 is installed, with flanges 6, in an existing pipeline system, not illustrated. The connection between the flanges 6 and the system consisting of the measuring tube 1 and the support pipe 2 is in the form of mounting sections referred to as suspensions 7. In addition, a central spring 8 provided in the center of the measuring tube 1 connects the measuring tube with the support pipe 2 to enhance the rigidity of the measuring tube 1, as described for instance in DE 42 00 060 A1.

Figure 2:
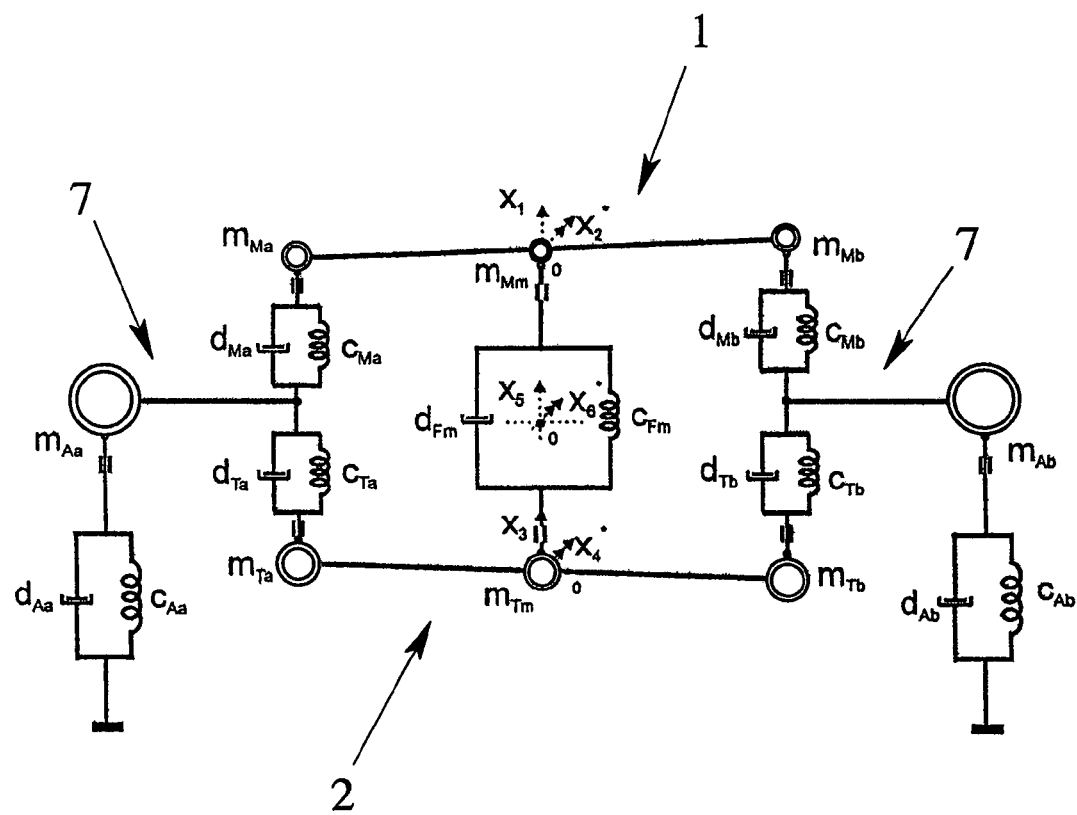
FIG. 2 illustrates one approach to a physical-mathematical model with concentrated substitute elements, according to the invention.

FIG. 2 shows a model insert, designed for the physical-mathematical model employed in this case, with concentrated substitute elements of the Coriolis mass flowmeter. The significant mechanical movements of the Coriolis mass flowmeter as shown in FIG. 1, represent the oscillations of the measuring tube 1 and the support pipe 2 in the first natural oscillating mode and in the second natural oscillating mode. They can be described on the basis of the oscillation pattern of the model shown in FIG. 2. The substitute elements marked M describe the respective effective mass, spring and attenuator of the measuring tube 1, the elements marked T describe the corresponding parameters of the support pipe 2. The substitute elements marked A for the respective mass, spring and attenuator are the substitute elements for the suspensions 7. The indices a and b represent the left and, respectively, the right half of the measuring tube 1, the support pipe 2 and the suspensions 7. The spring and attenuator marked Fm account for the fact that the measuring tube 1 is held in a central position by the central spring 8. Of course, in the absence of a central spring the corresponding references do not apply. The respective mass marked m accounts for the fact that a larger mass is involved in the oscillations in the first natural oscillating mode of the measuring tube and of the support pipe than in the oscillations of the second natural oscillating mode.

Corresponding in this model to an oscillation in the first natural oscillating mode is the cophasal translational movement of the respective mass of the measuring tube 1, the support pipe 2 and the suspensions 7. One rotation of the outer masses a and b around the axis of rotation $\chi_2$, $\chi_4$ and $\chi_6$ corresponds to one oscillation in the second natural oscillating mode. The mathematical description of the oscillation pattern of this system can be derived with the aid of the 2nd Lagrange equation as explained in detail at the end of this description.

Assuming that the oscillations of the measuring tube in its natural oscillating modes are mutually decoupled, that the movements of the support pipe are neglected and that the suspension does not move, the simplest model for the density measurement can be a 2nd order model that describes the oscillations of the measuring tube 1 only in its natural oscillating modes $v=1, 2$, etc. The correlated transfer function is as follows:

$$G_v(s) = \frac{k_v s}{s^2 + 2d_v \omega_{0v} s + \omega_{0v}^2} \quad (6)$$

An example of the parameters of this transfer function for the first natural oscillating mode is this:

$$k_1 = \frac{1}{m_{Ma} + m_{Mb} + m_{Mm}} = \frac{1}{m_1} \quad (7)$$

$$\omega_{01} = \sqrt{\frac{c_{Ma} + c_{Mb} + c_{Fm}}{m_{Ma} + m_{Mb} + m_{Mm}}} = \sqrt{c_1 k_1} = \sqrt{\frac{c_1}{m_1}} \quad (8)$$

$$d_1 = \frac{1}{2} \frac{d_{Ma} + d_{Mb} + d_{Fm}}{\sqrt{(c_{Ma} + c_{Mb} + c_{Fm})(m_{Ma} + m_{Mb} + m_{Mm})}} \quad (9)$$

The effective oscillating mass of the measuring tube 1 is composed of the mass of the empty measuring tube 1 and the mass of the flowing medium. If the mass and the volume of the empty measuring tube 1 are known, a density measurement is possible through the determination of the parameters of the transfer function. The density affects all three parameters of the transfer function, which is why measuring it via all three parameters of the transfer function is generally possible. To be sure, an exact measurement of the standardized attenuation d is a complex matter due to the rapid changes. Moreover, this parameter depends on the elasticity and attenuation constants which change during the ongoing operation and therefore must be measured in real-time.

The resonant frequency $\omega_{01}$ of the first mode fairly approximates the operating frequency of the Coriolis mass flowmeter as set by a phase regulator and is therefore a known entity. The drawback of the parameter $\omega_v$ is its dependence on the elasticity constant $c_v$. The parameter $k_v$ only depends on the oscillating masses but can be determined with the aid of an additional excitation.

All these considerations also apply in corresponding fashion to the basic concept of the higher modes of the measuring tube 1 and in particular to the second natural oscillating mode with this transfer function:

$$G_2(s) = \frac{k_2 s}{s^2 + 2d_2 \omega_{02} s + \omega_{02}^2} \quad (10)$$

The rule for the parameters of this transfer function is:

$$k_2 = \frac{1}{m_{Ma} + m_{Mb}} = \frac{1}{m_2} \quad (11)$$

$$\omega_{02} = \sqrt{\frac{c_{Ma} + c_{Mb}}{m_{Ma} + m_{Mb}}} = \sqrt{c_2 k_2} = \sqrt{\frac{c_2}{m_2}} \quad (12)$$

$$d_2 = \frac{1}{2} \frac{d_{Ma} + d_{Mb}}{\sqrt{(c_{Ma} + c_{Mb})(m_{Ma} + m_{Mb})}} \quad (13)$$

The following will explain in more detail the density measurement based on the parameters $\omega_{0v}$, $C_v$, $k_v$ and $m_v$. This takes into account the effective elasticity constant in the ongoing operation of the Coriolis mass flowmeter, which can be accomplished by a partial or full identification of the 2nd order model for one of the natural oscillating modes.

Direct Density Measurement Via the Effective Oscillating Mass $m_v$.

In order to determine the effective oscillating mass independent of the effective elasticity constant $c_v$ and to derive from that the density of the flowing medium, the Coriolis mass flowmeter is excited at one or several additional frequencies and the transfer function is measured. On that basis the parameters $k_v$, the mass $m_v$ and the rigidity or elasticity constant $c_v$ can be calculated.

The following describes a few preferred procedures in the natural oscillating mode 1 and natural oscillating mode 2, respectively. They can also be applied in corresponding fashion for other natural oscillating modes.

Density Measurement Via a Single Additional Excitation in the First Natural Oscillating Mode For the mass $m_1$ the defining equation, given an additional excitation $\omega_{Z1}$ after a few transformations, will be:

$$m_1 = \frac{\omega_{Z1}}{(\omega_{01}^2 - \omega_{Z1}^2)} \cdot \frac{\text{Im}\{G_1(j\omega_{Z1})\}}{\text{Im}\{G_1(j\omega_{Z1})\}^2 + \text{Re}\{G_1(j\omega_{Z1})\}^2} \quad (14)$$

Provided the space between the additional excitation and the resonant frequency is sufficiently large, the above Equation 14 is simplified into:

$$m_1 = \frac{\omega_{Z1}}{\text{Im}\{G_1(j\omega_{Z1})\}\omega_{01}^2} \quad (14a)$$

The effective elasticity constant is derived from:

$$c_1 = \omega_{01}^2 m_1 \simeq \frac{\omega_{Z1}}{\text{Im}\{G_1(j\omega_{Z1})\}} \quad (15)$$

In selecting the frequency position of the additional excitations it is necessary to weigh the trade-off between the highest possible amplitude of the measuring signals—with the frequency response of the transfer function $G_1$ and, respectively, $G_2$ declining above and below the resonant frequency at −20[dB] per decade—and an adequate distance from the operating frequency $\omega_{ov}$ in order to ensure good signal discrimination. This also applies to the preferred embodiment of the invention described below.

Density Measurement Via at Least One Additional Excitation in the First Natural Oscillating Mode and the Operational Stimulation in the First Natural Oscillating Mode The parameter $m_1$ can be determined, without recourse to the resonant frequency, in a manner corresponding to the operating frequency, through stimulation at a minimum of two additional frequencies $\omega_{ZA}$ and $\omega_{ZB}$ in the first natural oscillating mode. The defining equation for the mass $m_1$ will be:

$$m_1 = \frac{1}{\omega_{ZB}^2 - \omega_{ZA}^2} \frac{\omega_{ZA}\text{Im}\{G_1(j\omega_{ZA})\}}{\text{Im}\{G_1(j\omega_{ZA})\}^2 + \text{Re}\{G_1(j\omega_{ZA})\}^2} - \frac{1}{\omega_{ZB}^2 - \omega_{ZA}^2} \frac{\omega_{ZB}\text{Im}\{G_1(j\omega_{ZB})\}}{\text{Im}\{G_1(j\omega_{ZB})\}^2 + \text{Re}\{G_1(j\omega_{ZB})\}^2} \quad (16)$$

In theory, the position of the additional frequencies has no bearing on the density measurement. In reality, however, there is a minor dependence, making it desirable to tie the position of the additional frequencies to the operating frequency in symmetrically mirrored fashion.

Density Measurement Via Two Additional Excitations in the Second Natural Oscillating Mode The parameter $m_2$ can be determined as a measure for the density of the flowing medium via excitations at a minimum of two additional frequencies in the second natural oscillating mode. The defining equation for the mass $m_2$ will be:

$$m_2 = \frac{1}{\omega_{ZB}^2 - \omega_{ZA}^2} \frac{\omega_{ZA}\text{Im}\{G_2(j\omega_{ZA})\}}{\text{Im}\{G_2(j\omega_{ZA})\}^2 + \text{Re}\{G_2(j\omega_{ZA})\}^2} - \frac{1}{\omega_{ZB}^2 - \omega_{ZA}^2} \frac{\omega_{ZB}\text{Im}\{G_2(j\omega_{ZB})\}}{\text{Im}\{G_2(j\omega_{ZB})\}^2 + \text{Re}\{G_2(j\omega_{ZB})\}^2} \quad (17)$$

In the case of the additional excitations, one of the excitation frequencies could coincide with the resonant frequency. However, the additional frequencies are preferably selected in a symmetrically mirrored position relative to the resonant frequency $\omega_{01}$.

Indirect Density Measurement Via the Effective Elasticity Constant $c_v$

To fully utilize the advantages of a density measurement via the resonant frequency $\omega_{01}$ and via additional excitation, both processes are merged. This results in two preferred embodiments of the invention.

Density Measurement Via Two Additional Excitations in the Second Natural Oscillating Mode and the Operational Stimulation in the First Natural Oscillating Mode Since one or several additional excitations in the second natural oscillating mode are used for determining the sensitivity of the mass flow measurement, they might as well be utilized for the density measurement. As a first step, the elasticity constant of the second mode $c_1$ is determined by applying the additional excitation of the second mode. Given two additional frequencies $\omega_{ZA}$ and $2_{ZB}$, the defining equation after a few transformations will be:

$$c_2 = \frac{\omega_{ZA}\omega_{ZB}}{\omega_{ZB}^2 - \omega_{ZA}^2} \frac{\omega_{ZB}\text{Im}\{G_2(j\omega_{ZA})\}}{\text{Im}\{G_2(j\omega_{ZA})\}^2 + \text{Re}\{G_2(j\omega_{ZA})\}^2} - \frac{\omega_{ZA}\omega_{ZB}}{\omega_{ZB}^2 - \omega_{ZA}^2} \frac{\omega_{ZA}\text{Im}\{G_2(j\omega_{ZB})\}}{\text{Im}\{G_2(j\omega_{ZB})\}^2 + \text{Re}\{G_2(j\omega_{ZB})\}^2} \quad (18)$$

In the case of a single additional excitation at the frequency $\omega_{Z1}$, the resulting approximation will be:

$$c_2 = \frac{\omega_{Z1}}{\text{Im}\{G_1(j\omega_{Z1})\}} \quad (18a)$$

The relationship between the elasticity constants of two modi is:

$$c_1 = f(c_2, c_m, T, \ldots) \quad (19)$$

where in a specific case it will be:

$$c_1 = k \cdot c_2 + C_m(T) \quad (20)$$

The proportionality factor k is a design parameter and can be viewed as a constant. The elasticity constant $c_m$ essentially describes the condition of the central spring 8 whose elastic rigidity is corrected with the aid of the measured temperature.

This permits an indirect quantification of the effective elastic rigidity $c_1$ of mode 1. Since due to the phase correction in the operational stimulation the natural frequency $\omega_{01}$ is known by approximation, the effective oscillating mass in the first natural oscillating mode can be calculated based on the relationship $$m_1 = \frac{c_1}{\omega_{01}^2} \quad (21)$$

and can be used for the density measurement.

In typical Coriolis mass flowmeters the elasticity constant depends only to a minor extent on the oscillation amplitude, so that any effect of the oscillation amplitude on the density measurement can be ignored. For systems with a more dynamic amplitude and correspondingly greater amplitude dependence, off-line or even on-line modulation correction of the oscillation amplitude is preferred.

Density Measurement Via Two Additional Excitations in the First Natural Oscillating Mode and Operational Stimulation in the First Natural Oscillating Mode As an alternative, it is possible, by means of two additional excitations in the first natural oscillating mode, to directly determine the elasticity constant $c_1$ and to calculate the elastic rigidity $c_2$, needed for correcting the mass flow measurement, by rearranging Equation 20.

The defining equation for the elasticity constant $c_1$ is as follows:

$$c_1 = \frac{\omega_{ZA}\omega_{ZB}}{\omega_{ZB}^2 - \omega_{ZA}^2} \frac{\omega_{ZB}\text{Im}\{G_1(j\omega_{ZA})\}}{\text{Im}\{G_1(j\omega_{ZA})\}^2 + \text{Re}\{G_1(j\omega_{ZA})\}^2} - \frac{\omega_{ZA}\omega_{ZB}}{\omega_{ZB}^2 - \omega_{ZA}^2} \frac{\omega_{ZA}\text{Im}\{G_1(j\omega_{ZB})\}}{\text{Im}\{G_1(j\omega_{ZB})\}^2 + \text{Re}\{G_1(j\omega_{ZB})\}^2} \quad (22)$$

The following will explain the density measurement employing a 4th-order model according to another preferred embodiment of the invention. Here, the assumption of a mutual decoupling of the natural oscillating modes is abandoned.

Looking at the differential equations of the coupled systems of the first and second natural oscillating modes of the measuring tube, on which the mass flow measurement was based (described in more detail below), it becomes evident that the speed in this system is not maximized at natural frequency $\omega_{01}$ or $\omega_{02}$, but at the resonant frequencies of the coupled system.

Coupling of the second natural oscillating mode to the first natural oscillating mode of the measuring tube 1:

$$(m_{Ma}+m_{Mb}+m_{Mm})\ddot{x}_1+(d_{Ma}+d_{Mb}+d_m)$$
$$\dot{x}_1+(c_{Ma}+c_{Mb}+c_m)x_1+(m_{Ma}-m_{Mb})\ddot{x}_2+(d_{Ma}-d_{Mb})$$
$$\ddot{x}_2+(c_{Ma}-c_{Mb}) x_2=F_1 \quad (23)$$

Coupling of the first natural oscillating mode to the second natural oscillating mode of the measuring tube 1:

$$(m_{Ma}+m_{Mb})\ddot{x}_2+(d_{Ma}+d_{Mb})\dot{x}_2+(c_{Ma}+c_{Mb}) x_2+(m_{Ma}-m_{Mb})\ddot{x}_1+(d_{Ma}-d_{Mb})\dot{x}_1+(c_{Ma}-c_{Mb})x_1=F_2 \quad (24)$$

The resonant frequencies depend on both the lateral-excursion and acceleration couplings and the speed and mass-flow couplings. These couplings are factored-in either through direct identification of the fourth-order system including couplings via additional excitations, or by their compensation as in the case of a $k_{SA}$ compensation that is possible in mass flow measurements, and thus a decoupling and measurement of the density by means of a second-order system as described further above. With regard to a $k_{SA}$ compensation as is possible in mass flow measurements, specific reference is made to DE 100 02 635 A1, the objects and entire contents of which are hereby incorporated by reference herein.

The following will describe the effect of the movements of the support pipe on the density measurement. Here, the assumption is again made that the suspensions 7 do not move, while abandoning the assumption that the vibrations of the support pipe 2 relative to the measuring tube 1 are but negligible and that the movements of the measuring tube 1 and of the support pipe 2 are decoupled in terms of their natural oscillating modes. In this case, the combination of the natural oscillating modes of the measuring tube 1 and the support pipe 2 leads to various models of different orders.

Effect of the movements of the support pipe 2 on the first natural oscillating mode:

$$(m_{Ma}+m_{Mb}+m_{Mm})\ddot{x}_1+(d_{Ma}+d_{Mb}+d_m)$$
$$\dot{x}_1+(c_{Ma}+c_{Mb}+c_m)x_1+(m_{Ma}-m_{Mb})\ddot{x}_2+(d_{Ma}-d_{Mb})$$
$$\ddot{x}_2+(c_{Ma}-c_{Mb})x_2+(-d_m)\ddot{x}_3+(-c_m)x_3+(-d_{Ma}-d_{Mb})$$
$$\dot{x}_5+(-c_{Ma}-c_{Mb})x_5+(-d_{Ma}-d_{Mb})$$
$$\dot{x}_6+(-c_{Ma}+c_{Mb})x_6=F_1 \quad (25)$$

Effect of the movements of the support pipe 2 on the second natural oscillating mode:

$$(m_{Ma}+m_{Mb})\ddot{x}_2+(d_{Ma}+d_{Mb})$$
$$\dot{x}_2+(c_{Ma}+c_{Mb})x_2+(m_{Ma}-m_{Mb})\ddot{x}_1+(d_{Ma}-d_{Mb})$$
$$\dot{x}+(c_{Ma}-c_{Mb})x_1+(-d_{Ma}+d_{Mb})$$
$$\dot{x}_5+(-c_{Ma}+c_{Mb})x_5+(-d_{Ma}-d_{Mb})$$
$$\dot{x}_6+(-c_{Ma}-c_{Mb})x_6=F_2 \quad (26)$$

In this context it must be noted that the effect of the movements of the support pipe 2 on is the movements of the measuring tube 1 is indirectly modeled via the movement of the monovariants $\chi_5$ and $\chi_6$. Identifying these systems requires additional information on the distribution of the effective oscillating mass over the measuring tube 1 and the support pipe 2, respectively. Such information cannot be extracted from the oscillation sensors 5 shown in FIG. 1 since they only measure the relative movements of the measuring tube 1 and the support pipe 2. The assumption here is that the resonant points of the support pipe 2 are not located within the utilized frequency range of the measuring tube 1. If one still wants to gauge or monitor the effect of the movements of the support pipe 2 on the density measurement, additional sensors will be needed for the absolute measurement of the movements of the measuring tube and/or the support pipe. These movements within the monovariants $\chi_5$ and $\chi_6$ can be detected by suitable sensor types such as high-speed electromagnetic sensors, strain gauges or acceleration sensors, not illustrated in FIG. 1.

Finally, the following will discuss the effect of the movements of the suspensions 7 on the density measurement. The assumption here is that the suspensions 7 are capable of moving. If, as in this case, the movements of the measuring tube 1 relative to the support pipe 2 are measured for their impressed oscillations, an additional external excitation near the operational frequency can only contribute to uncertain results in density measurements. Yet, in general, an outside excitation of the support pipe 2 and the measuring tube 1 in the operating frequency range is largely prevented by virtue of the mechanical design of the Coriolis mass flowmeter. The effect of the movements of the suspensions 7 on the density measurement can be indirectly quantified via the movement of the monovariants $\chi_5$ and $\chi_6$. As described in the preceding paragraph, these movements can be detected by suitable sensors such as high-speed electromagnetic sensors, strain gauges or acceleration sensors.

Translational movement of the suspension along the $\chi_5$ axis:

$$(m_{Aa}+m_{Ab})\ddot{x}_5+(d_{Ma}+d_{Mb}+d_{Ta}+d_{Tb}+d_{Aa}+d_{Ab})$$
$$\dot{x}_5+(c_{Ma}+c_{Mb}+c_{Ta}+c_{Tb}+c_{Aa}+c_{Ab})x_5+(-d_{Ma}-d_{Mb})$$
$$\dot{x}_1+(-c_{Ma}-c_{Mb})x_1+(-d_{Ma}+d_{Mb})$$
$$\dot{x}_2+(-c_{Ma}+c_{Mb})x_2+(-d_{Ta}+d_{Tb})$$
$$\dot{x}_3+(-c_{Ta}-c_{Tb})x_3+(d_{Ta}+d_{Tb})$$
$$\dot{x}_4+(-c_{Ta}+c_{Tb})x_4+(m_{Aa}-m_{Ab})$$
$$\ddot{x}_6+(d_{Ma}-d_{Mb}+d_{Ta}-d_{Tb}+d_{Aa}-d_{Ab})$$
$$\dot{x}_6+(c_{Ma}-c_{Mb}+c_{Ta}-c_{Tb}+c_{Aa}-c_{Ab})x_6=F_5 \quad (27)$$

Rotational movement of the suspension around the $\chi_6$ axis:

$$(m_{Aa}+m_{Ab})\ddot{x}_6+(d_{Ma}+d_{Mb}+d_{Ta}+d_{Tb}+d_{Aa}+d_{Ab})$$
$$\dot{x}_6+(c_{Ma}+c_{Mb}+c_{Ta}+c_{Tb}+c_{Aa}+c_{Ab})x_6+(-d_{Ma}+d_{Mb})$$
$$\dot{x}_1+(-c_{Ma}+c_{Mb})x_1+(-d_{Ma}-d_{Mb})$$
$$\dot{x}_2+(-c_{Ma}-c_{Mb})x_2+(-d_{Ta}+d_{Tb})$$
$$\dot{x}_3+(-c_{Ta}+c_{Tb})x_3+(-d_{Ta}-d_{Tb})$$
$$\dot{x}_4+(-c_{Ta}-c_{Tb})x_4+(m_{Aa}-m_{Ab})$$
$$\ddot{x}_5+(d_{Ma}-d_{Mb}+d_{Ta}-d_{Tb}+d_{Aa}-d_{Ab})$$
$$\dot{x}_5+(c_{Ma}-c_{Mb}+c_{Ta}-c_{Tb}+c_{Aa}-c_{Ab})x_5=F_6 \quad (28)$$

The following concluding data reflect the energy balance and the motion equations referred to further above.

Energy Balance

Kinetic Energy:

$$E = \frac{1}{2}m_{Ma}(\dot{x}_1 + \dot{x}_2)^2 + \frac{1}{2}m_{Mb}(\dot{x}_1 - \dot{x}_2)^2 + \qquad (29)$$
$$\frac{1}{2}m_{Mm}\dot{x}_1^2 + \frac{1}{2}m_{Ta}(\dot{x}_3 + \dot{x}_4)^2 + \frac{1}{2}m_{Tb}(\dot{x}_3 - \dot{x}_4)^2 +$$
$$\frac{1}{2}m_{Tm}\dot{x}_3^2 + \frac{1}{2}m_{Aa}(\dot{x}_5 + \dot{x}_6)^2 + \frac{1}{2}m_{Ab}(\dot{x}_5 - \dot{x}_6)^2$$

Dissipated Energy Per Unit of Time:

$$D = \frac{1}{2}d_{Ma}(\dot{x}_1 + \dot{x}_2 - \dot{x}_5 - \dot{x}_6)^2 + \frac{1}{2}d_{Mb}(\dot{x}_1 - \dot{x}_2 - \dot{x}_5 + \dot{x}_6)^2 + \qquad (30)$$
$$\frac{1}{2}d_{Ta}(-\dot{x}_3 - \dot{x}_4 + \dot{x}_5 + \dot{x}_6)^2 + \frac{1}{2}d_{Tb}(-\dot{x}_3 + \dot{x}_4 + \dot{x}_5 - \dot{x}_6)^2 +$$
$$\frac{1}{2}d_{Aa}(\dot{x}_5 + \dot{x}_6)^2 + \frac{1}{2}d_{Ab}(\dot{x}_5 - \dot{x}_6)^2 + \frac{1}{2}d_m(\dot{x}_1 - \dot{x}_3)^2$$

Potential Energy:

$$U = \frac{1}{2}c_{Ma}(x_1 + x_2 - x_5 - x_6)^2 + \frac{1}{2}c_{Mb}(x_1 - x_2 - x_5 + x_6)^2 + \qquad (31)$$
$$\frac{1}{2}c_{Ta}(-x_3 - x_4 + x_5 + x_6)^2 + \frac{1}{2}c_{Tb}(-x_3 + x_4 + x_5 - x_6)^2 +$$
$$\frac{1}{2}c_{Aa}(x_5 + x_6)^2 + \frac{1}{2}c_{Ab}(x_5 - x_6)^2 + \frac{1}{2}c_m(x_1 - x_3)^2$$

Motion Equations $$\frac{d}{dt}\left(\frac{\partial E}{\partial \dot{q}_n}\right) - \frac{\partial E}{\partial q_n} + \frac{\partial D}{\partial \dot{q}_n} + \frac{\partial U}{\partial q_n} = F_n \qquad (32)$$

First natural mode—translational movement of the measuring tube along the $\chi_1$ axis:

$(m_{Ma}+m_{Mb}+m_{Mm})\ddot{x}_1+(d_{Ma}+d_{Mb}+d_m)$
$\phantom{()}\dot{x}_1+(c_{Ma}+c_{Mb}+c_m)x_1+(m_{Ma}-m_{Mb})\ddot{x}_2+(d_{Ma}-d_{Mb})$
$\phantom{()}\dot{x}_2+(c_{Ma}-c_{Mb})x_2+(-d_m)\ddot{x}_3+(-c_m)x_3+(-d_{Ma}-d_{Mb})$
$\phantom{()}\dot{x}_5+(-c_{Ma}-c_{Mb})x_5+(-d_{Ma}+d_{Mb})$
$\phantom{()}\dot{x}_6+(-c_{Ma}+c_{Mb})x_6=F_1$ \hfill (33)

Second natural mode—rotation of the measuring tube around the $\chi_2$ axis:

$(m_{Ma}+m_{Mb})\ddot{x}_2+(d_{Ma}+d_{Mb})$
$\phantom{()}\dot{x}_2+(c_{Ma}+c_{Mb})x_2+(m_{Ma}-m_{Mb})\ddot{x}_1+(d_{Ma}-d_{Mb})$
$\phantom{()}\dot{x}_1+(c_{Ma}-c_{Mb})x_1+(-d_{Ma}+d_{Mb})$
$\phantom{()}\dot{x}_5+(-c_{Ma}-c_{Mb})x_5+(-d_{Ma}-d_{Mb})$
$\phantom{()}\dot{x}_6+(-c_{Ma}-c_{Mb})x_6=F_2$ \hfill (34)

Translational movement of the support pipe along the $\chi_3$ axis:

$(m_{Ta}+m_{Tb}+m_{Tm})\ddot{x}_3+(d_{Ta}+d_{Tb}+d_m)$
$\phantom{()}\dot{x}_3+(c_{Ta}+c_{Tb}+c_m)x_3+(-d_m)\ddot{x}_1+(-c_m)x_1+(m_{Ta}-m_{Tb})$
$\phantom{()}\ddot{x}_4+(d_{Ta}-d_{Tb})\dot{x}_4+(c_{Ta}-c_{Tb})x_4+(-d_{Ta}-d_{Tb})$
$\phantom{()}\dot{x}_5+(-c_{Ta}-c_{Tb})x_5+(-d_{Ta}+d_{Tb})$
$\phantom{()}\dot{x}_6+(-c_{Ta}+c_{Tb})x_6=-F_1$ \hfill (35)

Rotation of the support pipe around the $X_4$ axis:

$(m_{Ta}+m_{Tb})\ddot{x}_4+(d_{Ta}+d_{Tb})\dot{x}_4+(c_{Ta}+c_{Tb})x_4+(m_{Ta}-m_{Tb})$
$\phantom{()}\ddot{x}_3+(d_{Ta}-d_{Tb})\dot{x}_3+(c_{Ta}-c_{Tb})x_3+(-d_{Ta}+d_{Tb})$
$\phantom{()}\dot{x}_5+(-c_{Ta}+c_{Tb})x_5+(-d_{Ta}-d_{Tb})$
$\phantom{()}\dot{x}_6+(-c_{Ta}-c_{Tb})x_6=-F_2$ \hfill (36)

Translational movement along the $X_5$ axis:

$(m_{Aa}+m_{Ab})\ddot{x}_5+(d_{Ma}+d_{Mb}+d_{Ta}+d_{Tb}+d_{Aa}+d_{Ab})$
$\phantom{()}\dot{x}_5+(c_{Ma}+c_{Mb}+c_{Ta}+c_{Tb}+c_{Aa}+c_{Ab})x_5+(-d_{Ma}-d_{Mb})$
$\phantom{()}\dot{x}_1+(-c_{Ma}-c_{Mb})x_1+(-d_{Ma}+d_{Mb})$
$\phantom{()}\dot{x}_2+(-c_{Ma}-c_{Mb})x_2+(-d_{Ta}-d_{Tb})$
$\phantom{()}\dot{x}_3+(-c_{Ta}-c_{Tb})x_3+(-d_{Ta}+d_{Tb})$
$\phantom{()}\dot{x}_4+(c_{Ta}+c_{Tb})x_4+(m_{Aa}-m_{Ab})$
$\phantom{()}\ddot{x}_6+(d_{Ma}-d_{Mb}+d_{Ta}-d_{Tb}+d_{Aa}-d_{Ab})$
$\phantom{()}\dot{x}_6+(c_{Ma}-c_{Mb}+c_{Ta}-c_{Tb}+c_{Aa}-c_{Ab})x_6=F_5$ \hfill (37)

Rotation around the $x_6$ axis:

$(m_{Aa}+m_{Ab})\ddot{x}_6+(d_{Ma}+d_{Mb}+d_{Ta}+d_{Tb}+d_{Aa}+d_{Ab})$
$\phantom{()}\dot{x}_6+(c_{Ma}+c_{Mb}+c_{Ta}+c_{Tb}+c_{Aa}+c_{Ab})x_6+(-d_{Ma}+d_{Mb})$
$\phantom{()}\dot{x}_1+(-c_{Ma}+c_{Mb})x_1+(-d_{Ma}-d_{Mb})$
$\phantom{()}\dot{x}_2+(-c_{Ma}-c_{Mb})x_2+(-d_{Ta}+d_{Tb})$
$\phantom{()}\dot{x}_3+(-c_{Ta}+c_{Tb})x_3+(-d_{Ta}-d_{Tb})$
$\phantom{()}\dot{x}_4+(-c_{Ta}-c_{Tb})x_4+(m_{Aa}-m_{Ab})$
$\phantom{()}\ddot{x}_5+(d_{Ma}-d_{Mb}+d_{Ta}-d_{Tb}+d_{Aa}-d_{Ab})$
$\phantom{()}\dot{x}_5+(c_{Ma}-c_{Mb}+C_{Ta}-c_{Tb}+c_{Aa}-c_{Ab})x_5=F_6$ \hfill (38)

The invention claimed is:

1. A method for operating a mass flowmeter that employs the Coriciple principle and through which flows a medium, said mass flowmeter incorporating a measuring tube through which the medium flows, said measuring tube being stimulated into oscillating at a minimum of two mutually different frequencies and/or in at least two mutually different natural oscillating modes and providing for the acquisition of the resulting oscillations of the measuring tube, including the step of measuring the density of the medium flowing through the measuring tube through an evaluation of the acquired oscillations of the measuring tube on the basis of a physical-mathematical model for the dynamics of the mass flowmeter, wherein the physical-mathematical model is at least of the 2nd order for the dynamics of the mass flowmeter.

2. The method as in claim 1, wherein the physical-mathematical model is capable of describing the oscillations of the mass flowmeter upon excitation of the measuring tube in its first natural oscillating mode and/or in its second natural oscillating mode.

3. The method as in claim 1, wherein for density measurements, the physical-mathematical model takes into account the coupling between the first natural oscillating mode and the second natural oscillating mode of the oscillations of the measuring tube.

4. The method as in claim 1, wherein for density measurements, the physical-mathematical model also takes into account, beside the measuring tube, the effect of at least one additional component of the mass flowmeter system, such as a support pipe and/or a suspension of the measuring tube in the mass flowmeter.

5. The method as in claim 1, including taking into account, via the physical-mathematical model, the effective elasticity constant of the measuring tube during ongoing operation.

6. The method as in claim 1, wherein, for the mass flow measurement, an operational stimulation of the measuring tube takes place in its first natural oscillating mode at a first frequency while an additional excitation of the measuring tube takes place in its first natural oscillating mode at a second frequency different from the first frequency, the resonant frequency of the measuring tube is determined in its first natural oscillating mode and the density of the medium flowing through the measuring tube is determined via the effective oscillating mass of the first natural oscillating mode based on the resonant frequency of the measuring tube in its first natural oscillating mode and on the acquired oscillations of the measuring tube resulting from the additional excitation of the measuring tube.

7. The method as in claims 1, including providing for a first additional excitation of the measuring tube in its first natural oscillating mode at a first frequency and a second additional excitation of the measuring tube in its first natural oscillating mode at a second frequency different from the first frequency, and determining the density of the medium flowing through the measuring tube via the effective oscillating mass of the first natural oscillating mode by means of the acquired oscillations of the measuring tube that result from the two additional excitations of the measuring tube.

8. The method as in claim 7, wherein for the mass flow measurement, an operational stimulation of the measuring tube in its first natural oscillating mode is generated by a third frequency that differs from the first frequency and from the second frequency and the density of the medium flowing through the measuring tube is measured via the resonant frequency of the measuring tube in its first natural oscillating mode and the effective elasticity constants determined through the additional excitations.

9. The method as in claim 1, wherein a first additional excitation of the measuring tube takes place in its second natural oscillating mode at a first frequency and a second additional excitation of the measuring tube takes place in its second natural oscillating mode at a second frequency different from the first frequency, and the density of the medium flowing through the measuring tube is measured via the effective oscillating mass of the second natural oscillating mode by means of the acquired oscillations of the measuring tube resulting from the two additional excitations.

10. The method as in claim 9, wherein an operational stimulation of the measuring tube takes place in its first natural oscillating mode at a third frequency that differs from the first frequency and from the second frequency, and the density of the medium flowing through the measuring tube is measured via the resonant frequency of the measuring tube in its first natural oscillating mode and the effective elasticity constants established via the effective elasticity constants determined through the additional excitations.

11. The method as in claim 1, wherein the temperature in the mass flowmeter is measured to take into account the temperature dependence of the functionality of such mass flowmeter components as an oscillation generator for the measuring tube and/or an oscillation sensor for the measuring tube.

12. The method as in claim 1, wherein the temperature of the measuring tube is measured to take into account a thermally induced change in the volume of the measuring tube during the density measurement.

13. The method as in claim 1, wherein the pressure in the measuring tube is measured to take into account a pressure-dependent change in the volume of the measuring tube during the density measurement.

14. A method for operating a mass flowmeter that employs the Coriolis principle and through which flows a medium, said mass flowmeter incorporating a measuring tube through which the medium flows, said measuring tube being stimulated into oscillating at a minimum of two mutually different frequencies and/or in at least two mutually different natural oscillating modes and providing for the acquisition of the resulting oscillations of the measuring tube, including the step of measuring the density of the medium flowing through the measuring tube through an evaluation of the acquired oscillations of the measuring tube on the basis of a physical-mathematical model for the dynamics of the mass flowmeter, wherein the physical-mathematical model is capable of describing the oscillations of the mass flowmeter upon excitation of the measuring tube in its first natural oscillating mode and/or in its second natural oscillating mode.

15. A method for operating a mass flowmeter that employs the Coriolis principle and through which flows a medium, said mass flowmeter incorporating a measuring tube through which the medium flows, said measuring tube being stimulated into oscillating at a minimum of two mutually different frequencies and/or in at least two mutually different natural oscillating modes and providing for the acquisition of the resulting oscillations of the measuring tube, including the step of measuring the density of the medium flowing through the measuring tube through an evaluation of the acquired oscillations of the measuring tube on the basis of a physical-mathematical model for the dynamics of the mass flowmeter, wherein for density measurements, the physical-mathematical model takes into account the coupling between the first natural oscillating mode and the second natural oscillating mode of the oscillations of the measuring tube.

* * * * *